United States Patent [19]

Holtkamp, Sr.

[11] Patent Number: Plant 6,437

[45] Date of Patent: Dec. 6, 1988

[54] AFRICAN VIOLET PLANT NAMED BARBADOS

[76] Inventor: Reinhold Holtkamp, Sr., Werther Strasse 112, D4294 Isselburg, Fed. Rep. of Germany

[21] Appl. No.: 21,736

[22] Filed: Mar. 4, 1987

[51] Int. Cl.[4] ..... A01H 5/00

[52] U.S. Cl. ..... Plt./69

[58] Field of Search ..... Plt. 69

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of African violet named Barbados, as described and illustrated, and particularly by its single blue violet flower with white edges; strong, upright flower stems that curve toward the center to form a bouquet above the leaves; profuse flowering, vigorous growth habit, flowering 9–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Barbados.

The new cultivar was referred to during the breeding and selection process by the designation H77/9, and is a product of a planned breeding program. The new cultivar was originated from a cross made by me in the controlled breeding program in Isselburg, Federal Republic of Germany. The female, or seed parent, was a cultivar designated D198/5 Blue Single. The male, or pollen parent, was a cultivar designated GG18 Light Blue Star.

Barbados was discovered and selected by me in 1983 as a flowering plant within the progeny of the stated cross in a controlled environment in Isselburg, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Barbados has not been observed under all possible environmental conditions. The phenotype may vary significantly with variations in environment such as temperature, light intensity and day length. The following observations, measurements and values describe the new cultivar as grown in Haffen, Federal Republic of Germany and Nashville, Tenn., under greenhouse conditions which closely approximate those generally used in commercial practice.

The following traits have been repeatedly observed and are determined to be basic characteristics of Barbados which in combination distinguish this African violet as a new and distinct cultivar:

(1) Strong, upright flower stems curving toward the center.

(2) First flash of flowers form a tight bouquet above the leaves.

(3) The flower head builds in three visible incremental steps that flower 14 days apart.

(4) Profuse flowering.

(5) Each plant carries up to 10 and more upright flower stems each of which carries 8–12 flowers.

(6) Vigorous grower.

(7) Plant saleable 9–10 weeks after potting.

(8) Medium green velvety leaves, slightly hairy.

(9) Long-lasting non-dropping single flowers.

(10) Seed capsule pushes slightly through.

(11) After maturity the flowers dry off, and remain on the peduncle without becoming infected by botrytis.

(12) The purple flowers have a white margin around the petals.

Barbados is similar in certain respects to Wyoming, disclosed in U.S. Plant Pat. No. 5,022. The flower arrangement and upright stems are similar. However, the flower color of Barbados is a more blue violet, and there are white edges around the petals.

The accompanying color photographic drawing shows a typical specimen plant of the new cultivar. The colors appearing in the photograph are as true as possible with color illustrations of this type.

In the following description, color references are made to The Royal Horticultural Society Color Chart (R.H.S.), except where general colors of ordinary significance are referred to. Color values were taken under natural sunlight conditions at approximately 1:00 in Nashville, Tenn.

Botanical classification: *Saintpaulia ionantha,* Ramat., cv. Barbados.

Parentage:

*Male parent.*—GG18 Light Blue Star.

*Female parent.*—D 198/5 Blue Single.

Propagation: The new cultivar holds its distinguishing characteristics through successive propagations by leaf cuttings.

Plant: From 7 cm to 10 cm tall when grown in pots, and approximately 22 cm in diameter when fully grown.

*Leaves.*—General form: Oval. Diameter: 65–70 mm wide and 85–95 mm long. Texture: Leatherlike. Aspect: Velvet, slightly hairy. Veins: Underside: well pronounced, light green shiny, in between the veins and underside is purplish green. Color (upper side): Green Group 137 A. Color (under side): Green Group 148 between C and D. Petiole: Strong, upright brownish purple, hairy.

Flowers.—Buds: Bell-shaped 8–10 mm before opening. Sepals: Five (5) spear shaped, hairy. Calyx: Shape: Funnel-shaped. Aspect: Spear-shaped, hairy. Peduncle: Character: Strong, upright, hairy. Color: Brownish. Individual flowers: Size: 35–40 mm. Shape: Single violet-shaped, slightly waved. Color (upper side): Violet blue 93B. Color (under side): Violet blue 92A. Borne: Stems carry 8–12 flowers on strong, upright wirelike peduncles. Flowering habit: Flowers 8–9 weeks after potting, with slightly open flower head forming above the leaves. The flower head builds incrementally in three steps which flower 14 days apart.

*Reproductive organs.*—Stamens: 2. Anthers: Two stamens, with four anther cells. Filaments: 5 mm. Pollen Color: Yellow 7A. Styles: 6 mm dark purple.

*Roots.*—Normally developed, white when young, turning slightly brownish when older.

Disease resistance: Good.

General observations: Barbados is a vigorous grower, with attractive velvety medium green leaves. Out of the center, 10 and more strong flower stems appear that are slightly bent toward the center, carrying 8–12 and more single blue flowers which are slightly wavy with white margins. The fully developed flower head does not have a tight bouquet. Approximately 9–10 weeks after potting the plant is saleable. The flowers are long-lasting and non-dropping and the seed capsule pushes through.

I claim:

1. A new and distinct cultivar of African violet named Barbados, as described and illustrated, and particularly characterized by its single blue violet flower and white edges; strong, upright flower stems that curve toward the center to form a bouquet above the leaves; profuse flowering, vigorous growth habit, flowering 9–10 weeks after potting, and its long-lasting and non-dropping flowers.

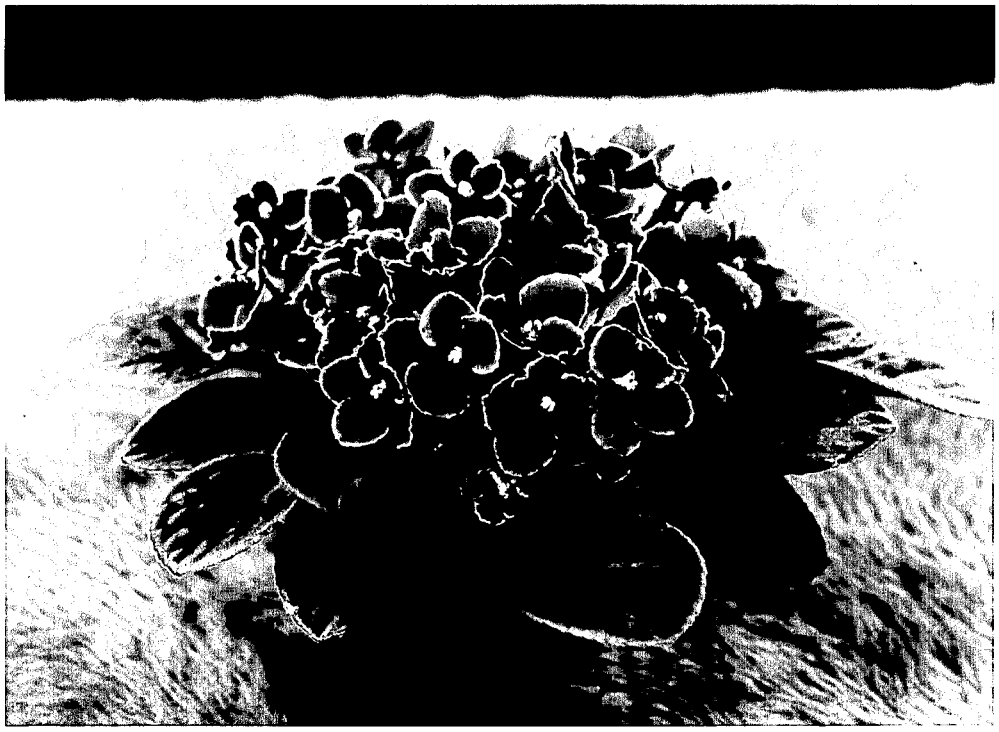

* * * * *